United States Patent
Lerch

(10) Patent No.: US 6,962,591 B2
(45) Date of Patent: *Nov. 8, 2005

(54) DEVICE FOR POSTOPERATIVE FIXATION BACK INTO THE CRANIUM OF A PLUG OF BONE REMOVED THEREFROM DURING A SURGICAL OPERATION

(76) Inventor: Karl-Dieter Lerch, Nordstrasse 16, D-58452 Bundesrepublik (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/793,814

(22) Filed: Mar. 8, 2004

(65) Prior Publication Data

US 2004/0172029 A1 Sep. 2, 2004

Related U.S. Application Data

(63) Continuation of application No. 10/011,379, filed on Oct. 22, 2001, now Pat. No. 6,726,688, which is a continuation of application No. 09/827,861, filed on Apr. 6, 2001, now Pat. No. 6,328,743, which is a continuation of application No. 09/494,599, filed on Jan. 31, 2000, now Pat. No. 6,270,500, which is a continuation of application No. 09/088,175, filed on Jun. 1, 1998, now Pat. No. 6,068,631, which is a continuation of application No. 08/790,071, filed on Jan. 28, 1997, now Pat. No. 5,800,436.

(51) Int. Cl.$^7$ .............................................. A61B 17/68
(52) U.S. Cl. ............................ 606/72; 606/73; 606/213
(58) Field of Search ............................ 606/60, 69–73, 606/75, 151, 213, 215, 216, 232; 411/145, 155, 156, 158, 163, 338, 339, 352, 353, 525–527, 533, 544

(56) References Cited

U.S. PATENT DOCUMENTS

| | | |
|---|---|---|
| 276,135 A | 4/1883 | Cooley |
| 741,747 A | 10/1903 | Walz |
| 1,105,105 A | 7/1914 | Sherman |

(Continued)

FOREIGN PATENT DOCUMENTS

| | | |
|---|---|---|
| DE | 1 089 116 | 9/1960 |
| DE | 2 125 556 | 6/1972 |
| DE | 28 06 609 B1 | 7/1979 |
| DE | 85 23 003.8 | 4/1986 |
| DE | 296 14 920 U1 | 10/1996 |
| DE | 296 14 922 U1 | 10/1996 |

(Continued)

OTHER PUBLICATIONS

Codman & Shurtleff, Inc., catalog entitled, "Neurosurgical Quality Instruments," cover page and pp. 10–13(TODD Burr hole buttons) (five pages total).

Codman & Shurtleff, Inc., publication showing ACCU-FLO™ Burr hole buttons (four pages total).

U. Heim & K.M. Pfeiffer,"Internal Fixation of Small Fractures," Technique Recommended by the AO–ASIF Group, Springer–Verlag Berlin Heidelberg (1974, 1982, & 1988), p. 60.

(Continued)

Primary Examiner—David O. Reip
(74) Attorney, Agent, or Firm—Kenyon & Kenyon

(57) ABSTRACT

A device for rapid reattachment of a bone flap to a cranium after a surgical operation is provided. The device comprises a pin comprising an elongated shaft, an inner disk and an outer disk. At least the outer disk comprises a central bore. The pin and inner disk are adapted to be assembled together to form a pin and inner disk assembly such that the inner disk is located at one end of the pin. The outer disk is adapted to be mounted on the shaft of the pin with the shaft of the pin extending through the central bore of the outer disk. The device is operated by (i) positioning the inner disk on the inside of the cranium with the shaft of the pin extending through the kerf between the bone flap and the cranium, (ii) forcing the outer disk downwardly on the shaft of the pin toward the inner disk until the outer disk securely engages the outside of the bone flap and the cranium, such that the bone flap is securely held in place between the inner disk and the outer disk, and (iii) trimming off an excess portion of the shaft extending out beyond the outer disk.

24 Claims, 4 Drawing Sheets

U.S. PATENT DOCUMENTS

| | | |
|---|---|---|
| 1,390,485 A | 9/1921 | Bell |
| 1,510,416 A | 9/1924 | Pietz et al. |
| 1,616,232 A | 2/1927 | Roberts et al. |
| 1,724,394 A * | 8/1929 | Chamberlain ............... 403/281 |
| 1,849,604 A * | 3/1932 | Weatherhead, Jr. ......... 411/352 |
| 1,890,348 A * | 12/1932 | Weatherhead, Jr. ......... 411/352 |
| 2,077,804 A | 4/1937 | Morrison |
| 2,238,238 A | 4/1941 | Westrope |
| 2,329,471 A | 9/1943 | King |
| 2,489,870 A | 11/1949 | Dzus |
| 2,494,229 A | 6/1950 | Collison |
| 2,511,051 A | 6/1950 | Dzus |
| 2,576,649 A | 11/1951 | Slind |
| 2,791,868 A | 5/1957 | Viken |
| 2,846,744 A | 8/1958 | Becker |
| 3,019,887 A | 2/1962 | Lowden |
| 3,281,171 A | 10/1966 | Hughes |
| 3,547,114 A | 12/1970 | Haboush |
| 3,712,357 A | 1/1973 | Corbett et al. |
| 3,741,205 A | 6/1973 | Markolf et al. |
| 3,779,240 A | 12/1973 | Kondo |
| 3,790,507 A | 2/1974 | Hodosh |
| 3,875,936 A | 4/1975 | Volz |
| 4,020,734 A * | 5/1977 | Bell ............................ 411/10 |
| 4,033,243 A | 7/1977 | Kirrish et al. |
| 4,116,200 A | 9/1978 | Braun et al. |
| 4,219,015 A | 8/1980 | Steinemann |
| 4,275,490 A | 6/1981 | Bivins |
| 4,360,025 A | 11/1982 | Edwards |
| 4,503,848 A | 3/1985 | Caspar et al. |
| 4,643,610 A | 2/1987 | Bien |
| 4,651,724 A | 3/1987 | Berentey et al. |
| 4,669,473 A | 6/1987 | Richards et al. |
| 4,683,878 A | 8/1987 | Carter |
| 4,688,561 A | 8/1987 | Reese |
| 4,793,335 A | 12/1988 | Frey et al. |
| 4,802,477 A | 2/1989 | Gabbay |
| 4,875,815 A | 10/1989 | Phillips, II |
| 4,903,691 A | 2/1990 | Heinl |
| 4,905,679 A | 3/1990 | Morgan |
| 4,905,680 A | 3/1990 | Tunc |
| 4,923,471 A | 5/1990 | Morgan |
| 4,988,351 A | 1/1991 | Paulos et al. |
| 5,013,316 A | 5/1991 | Goble et al. |
| 5,087,202 A | 2/1992 | Krenkel |
| 5,098,433 A | 3/1992 | Freedland |
| 5,139,497 A | 8/1992 | Tilghman et al. |
| 5,167,665 A | 12/1992 | McKinney |
| 5,196,016 A | 3/1993 | Buser et al. |
| 5,201,737 A | 4/1993 | Leibinger et al. |
| 5,250,049 A | 10/1993 | Michael |
| 5,268,001 A | 12/1993 | Nicholson et al. |
| 5,269,784 A | 12/1993 | Mast |
| 5,342,393 A | 8/1994 | Stack |
| 5,346,492 A | 9/1994 | Morgan |
| 5,350,399 A | 9/1994 | Erlebacher et al. |
| 5,352,229 A | 10/1994 | Goble et al. |
| 5,372,598 A | 12/1994 | Luhr et al. |
| 5,433,053 A | 7/1995 | Tulloch |
| 5,433,719 A | 7/1995 | Pennig |
| 5,468,242 A | 11/1995 | Reisberg |
| 5,501,685 A | 3/1996 | Spetzler |
| 5,549,620 A | 8/1996 | Bremer |
| 5,578,036 A | 11/1996 | Stone et al. |
| 5,601,558 A | 2/1997 | Torrie et al. |
| 5,669,912 A | 9/1997 | Spetzler |
| 5,707,373 A | 1/1998 | Sevrain et al. |
| 5,722,976 A | 3/1998 | Brown |
| 5,800,436 A | 9/1998 | Lerch |
| 5,916,200 A | 6/1999 | Eppley et al. |
| 5,928,244 A | 7/1999 | Tovey et al. |

FOREIGN PATENT DOCUMENTS

| | | |
|---|---|---|
| DE | 296 14 923 U1 | 10/1996 |
| DE | 296 14 921 | 11/1996 |
| EP | 0 290 138 A2 | 11/1988 |
| EP | 0 433 852 A1 | 6/1991 |
| EP | 0 510 390 | 10/1992 |
| FR | 2 386 301 | 11/1978 |
| FR | 2 631 539 | 11/1989 |
| FR | 2 703 239 A1 | 10/1994 |
| JP | 05-21954 | 1/1993 |
| JP | 05-220174 | 8/1993 |
| SU | 1512584 A1 | 10/1989 |
| SU | 1600713 | 10/1990 |
| SU | 1655477 A1 | 6/1991 |
| WO | WO 97/29708 | 8/1997 |

OTHER PUBLICATIONS

M.E. Mueller, M. Allgower and H. Willenegger, "Manual of Internal Fixation," Technique Recommended by the AO–Group, Springer–Verlag Berlin Heidelberg (1970), pp. 46–47.

Publication entitled, "For the Few Who Know The Difference," published by TiMesh, Inc.

Hans G. Luhr, M.D., D.M.D., "Indications for Use of a Microsystem for Internal Fixation in Craniofacial Surgery," J. of Craniofacial Surgery, vol. 1, No. 1 (Jan. 1990), pp. 35–52.

Howmedica International, Inc., "Vitallium—Verschledene Implantate," p. 54.

Publication entitled, "Leibinger," by Leibinger LP (copyright 1995).

Walter Lorenz Surgical, Inc., "Surgical Instrument Catalog 5$^{th}$ Edition," pp. 10–11 (copyright 1993).

Walter–Lorenz Surgical, Inc., "1.5/2.0mm Combination Titanium Osteosynthesis System"(copyright 1994).

Expert Report of Lawrence M. Shuer, M.D., Regarding Invalidity of Claims 1–13 of U.S. Patent No. 6,068,631 from Aesculap AG & CO. KG, Aesculap, Inc., and Karl–Dieter Lerch, M.D. v. Walter Lorenz Surgica, Inc., Case No. C–00–02394–MJJ (N.D. Cal.).

Expert Report of Donald O. Cox, Ph.D., Regarding In Validity of the Asserted Claims of U.S. Patent No. 6,068,631 from Aesculap AG & CO. KG, Aesculap, Inc., and Karl–Dieter Lerch, M.D. v. Walter Lorenz Surgical, Inc., Case No. C–00–02394–MJJ (N.D. Cal.).

Expert Witness Report of Mark E. Nusbaum from Aesculap AG & CO. KG, Aesculap, Inc., and Karl–Dieter Lerch, M.D. v. Walter Lorenz Surgical, Inc., Case No. C–00–02394–MJJ (N.D. Cal.).

Rebuttal Expert Report of Andrew S. Douglas, Ph.D. from Aesculap AG & CO. KG, Aesculap, Inc. and Karl–Dieter Lerch, M.D. v. Walter Lorenz Surgical, Inc., Case No. C–00–02394–MJJ (N.D. Cal.).

Rebuttal Expert Report of Donald Philip Magison, M.D. from Aesculap AG & CO. KG, Aesculap, Inc., and Karl–Dieter Lerch, M.D. v. Walter Lorenz Surgical, Inc., Case No. C–00–02394–MJJ (N.D. Cal.).

Notice of Motion and Motion by Defendant Lorenz for Summary Judgment of Invalidity, and the attached 19–page Defendant Lorenz's Memorandum of Points and Authorities in Support of its Motion for Summary Judgment of Invalidity from Aesculap AG & CO. KG. Aesculap, Inc., and Karl–Dieter Lerch, M.D. v. Walter Lorenz Surgical, Inc., Case No. C–00–02394–MJJ (N.D. Cal.).

Declaration of Lawrence M. Shuer, M.D., in Support of Lorenz's Motion for Summary Adjudication of Invalidity U.S. Patent No. 6,068,631 from Aesculap AG & CO. KG, Aesculap, Inc., and Karl–Dieter Lerch, M.D. v. Walter Lorenz Surgical, Inc., Case No. C–00–02394–MJJ (N.D. Cal.).

Declaration of Donald O. Cox, Ph.D., Regarding Invalidity of the Asserted Claims of U.S. Patent No. 6,068,631 from Aesculap AG & CO. KG, Aesculap, Inc., and Karl–Dieter Lerch, M.D. v. Walter Lorenz Surgical, Inc., Case No. C–00–02394–MJJ (N.D. Cal.).

Declaration of William D. Noonan, M.D. from Aesculap AG & CO. KG, Aesculap, Inc., and Karl–Dieter Lerch, M.D. v. Walter Lorenz Surgical, Inc., Case No. C–00–02394–MJJ (N.D. Cal.).

Stipulation and Order of Dismissal with Prejudice from Aesculap AG & CO. KG, Aesculap, Inc., and Karl–Dieter Lerch, M.D. v. Walter Lorenz Surgical, Inc., Case No. C–00–02394–MJJ (N.D. Cal.).

* cited by examiner the parts of the joint, with the shaft of the pin projecting out of the kerf between the plug and the rest of the cranium. The outer disk is then mounted over the section of pin projecting out of the kerf. The two disks are then approached until their teeth bite into the edges of both the plug and of the rest of the cranium. The second disk is then secured to the shaft.

DEVICE FOR POSTOPERATIVE FIXATION BACK INTO THE CRANIUM OF A PLUG OF BONE REMOVED THEREFROM DURING A SURGICAL OPERATION

This application is a continuation of U.S. patent application Ser. No. 10/011,379, filed Oct. 22, 2001 now U.S. Pat. No. 6,726,688, which is a continuation of prior U.S. patent application Ser. No. 09/827,861, filed Apr. 6, 2001, now U.S. Pat. No. 6,328,743 B2, which is a continuation of prior U.S. patent application Ser. No. 09/494,599, filed Jan. 31, 2000, now U.S. Pat. No. 6,270,500 B1, which is a continuation of U.S. patent application Ser. No. 09/088,175, filed Jun. 1, 1998, now U.S. Pat. No. 6,068,631, which is a continuation of U.S. patent application Ser. No. 08/790,071, filed Jan. 28, 1997, now U.S. Pat. No. 5,800,436.

BACKGROUND OF THE INVENTION

The present background of the invention concerns a device for postoperative fixation back into the cranium of a plug of bone removed therefrom during a surgical operation.

It is often necessary during brain surgery to remove a plug of bone from the cranium to provide the surgeon with access to the field of operation. The plug is sawed out and must be replaced in the cranium after the operation and fixed thereto. Such plugs have long been fixed back into the rest of the cranium by suturing with loops of steel wire that extend through both and then twisting together the projecting ends of the emplaced loops. The contact between the plug and the rest of the cranium is relatively unstable, however. The two halves do not fuse together very well. The scalp can also become inflamed. Another drawback to such an approach is that the wire considerably distorts the images obtained in postoperative computerized tomography and accordingly impedes definitive interpretation of the soft structures of the brain. Although using nonresorbable and physiologically compatible thread instead of wire does eliminate the last-mentioned drawback, the fixation of the plug to the rest of the skull is still unstable. The two parts can also be fixed with thin plates of compatible metal, titanium for instance (EP A 0 510 390). Such plates bridge the abutment between the parts and are screwed to both, also closing off bores introduced into the cranium prior to section. This approach, however, is also not very satisfactory. It is both complicated and time-consuming and hence not inexpensive.

SUMMARY OF THE INVENTION

With the aforesaid state of the art as a point of departure, the object of the present invention is a simpler and more rapid device for accurate and permanent postoperative fixation back into the cranium of a plug of bone removed therefrom during a surgical operation.

This object is attained in accordance with the present invention in a device of the aforesaid genus comprising a pin and two concavoconvex disks of a physiologically compatible metal or metal compound. The pin has a flat head at one end and one of the disks comes to rest against the head. Each disk has row of teeth extending along the edge of the concave side and a bore through the center. The shaft of the pin fits into the bore. The disks can be mounted on the shaft with the teeth on each one facing the teeth on the other. The second disk can be fastened to the shaft.

The inner disks in the aforesaid fixation device in accordance with the present invention are secured to the pins in the vicinity of the head. The disks are then inserted through a slightly larger recess in the circumference of the plug, below the parts of the joint, with the shaft of the pin projecting out of the kerf between the plug and the rest of the cranium. The outer disk is then mounted over the section of pin projecting out of the kerf. The two disks are then approached until their teeth bite into the edges of both the plug and of the rest of the cranium. The second disk is then secured to the shaft.

Titanium is particularly appropriate for the physiologically compatible metal. Such titanium alloys as $Ti_6A_6Va$ are also appropriate. A device made of titanium is of advantage because it will not distort postoperative computerized-tomography images. The inner disk can be mounted more stable on the shaft of the pin if the transition between the head of the pin and the shaft is conical and dimensioned to ensure that a disk resting against the head will be forced tight around the shaft. Slits can also extend radially outward from the bore through the first disk to be mounted on the shaft. The center of the disk can be depressed. Areas can be removed from the disks at regular intervals between the bore and the edge to conserve material. The device can be applied to the two halves of bone by a procedure similar in principle to blind riveting. Notches can accordingly be introduced into each shaft to prevent the second disk mounted thereon from sliding away from the head of the pin. If the second disk on the shaft is deformed in a direction opposite that of its concavoconvexity, the deformation alone will secure it to the shaft by compression. The shaft can also be threaded and accommodate a nut. The nut can be tightened against the second disk. The second disk will in every case be displaced until its teeth engage the two halves of the joint, creating the desired fixation of the plug back into the rest of the cranium at the adjacent edges.

The novel device can be easily and rapidly manipulated and accomplishes the desired accurate and permanent postoperative fixation back into the cranium of a plug of bone removed therefrom during a surgical operation.

BRIEF DESCRIPTION OF THE DRAWING

The present invention will now be specified with reference to the accompanying drawing wherein.

DESCRIPTION OF THE PREFERRED EMBODIMENTS

Figure 1:
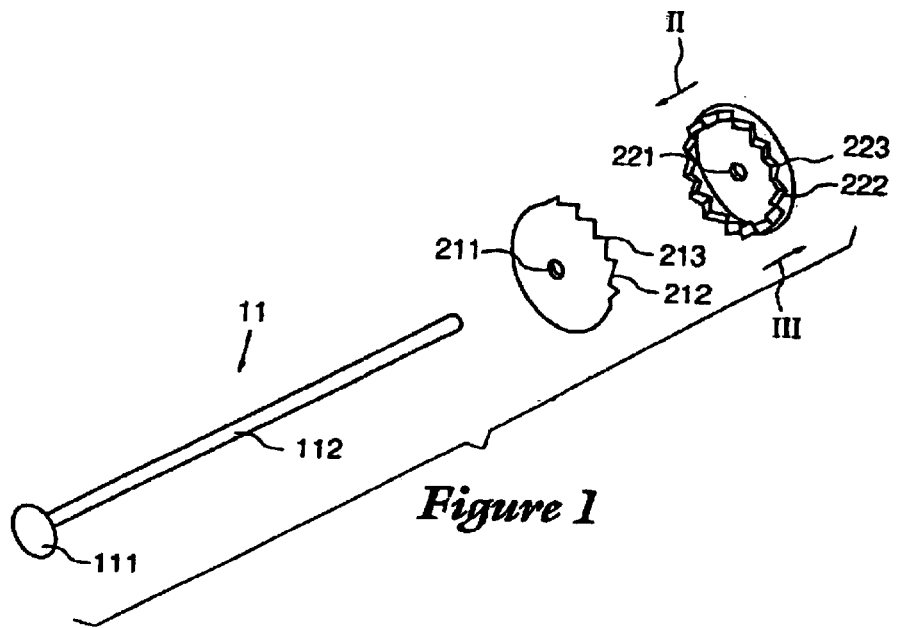
FIG. 1 is an exploded view of the device in accordance with the present invention.
Figure 4:
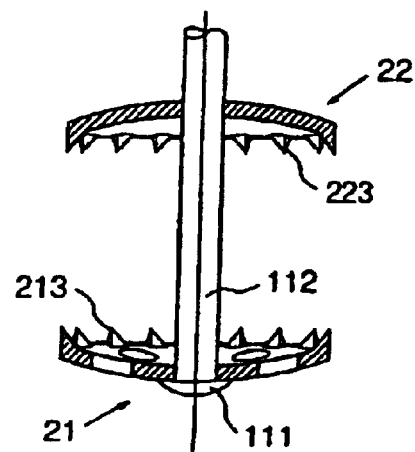
FIG. 4 is a longitudinal section of the components of the device assembled.

A device for postoperatively fixing back into the cranium a plug of bone removed therefrom during a surgical operation comprises a pin 11 and two concavoconvex disks 21 and 22. The pin comprises a shaft 112 and a head 111, Disk 21, the inner disk, is mounted on the shaft first and comes to rest against the inner surface of the plug and of the rest of the cranium that are to be united. Disk 22, the outer disk, is mounted on the shaft next and comes to rest against the outer surface of the plug and the rest of the cranium. There is a hole 211 through the center of each disk 21 and a hole 221 through the center of each disk 22. The shaft 112 of pin 11 extends through the holes 211 and 221 of the disks in the assembled device. A row of teeth 213 extends along the edge 212 of the concave side of disk 21, and a row of teeth 223 extends along the edge 222 of the concave side of disk 22. As will be evident from FIGS. 1 and 4, disks 21 and 22 are mounted on the shaft 112 of pin 11 with their teeth facing each other.

Figure 2:
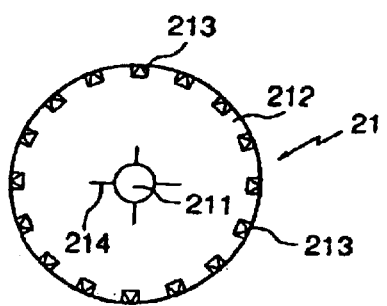
FIG. 2 is a view in the direction indicated by arrow II in FIG. 1 of one embodiment of the first disk mounted over the shaft of the pin.
Figure 3:
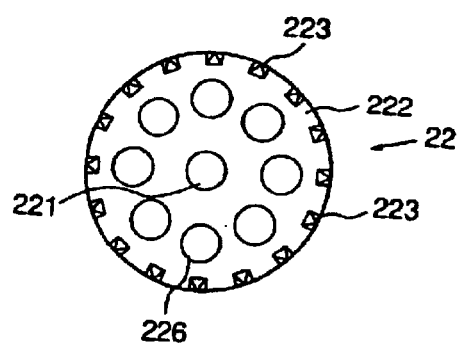
FIG. 3 is a view in the direction indicated by arrow III in FIG. 1 of one embodiment of the second disk mounted over the shaft of the pin.

Shaft 112 fits tightly in the hole 211 through disk 21. Any disk can be provided as illustrated in FIG. 2 with slits 214 extending radially outward from the hole 211 through its center. If the transition between the head 111 and the shaft 112 of pin 11 is conical, slits 214 will as is desirable accurately position the disk in relation to the pin, both of which will accordingly support both the plug and the rest of the cranium once the device has been emplaced. The area between the hole through the center of any disk and its circumference can also be provided as illustrated in FIG. 3 with perforations 226 to conserve material and decrease weight. Each disk can have both slits 214 and perforations 226.

Figure 5:
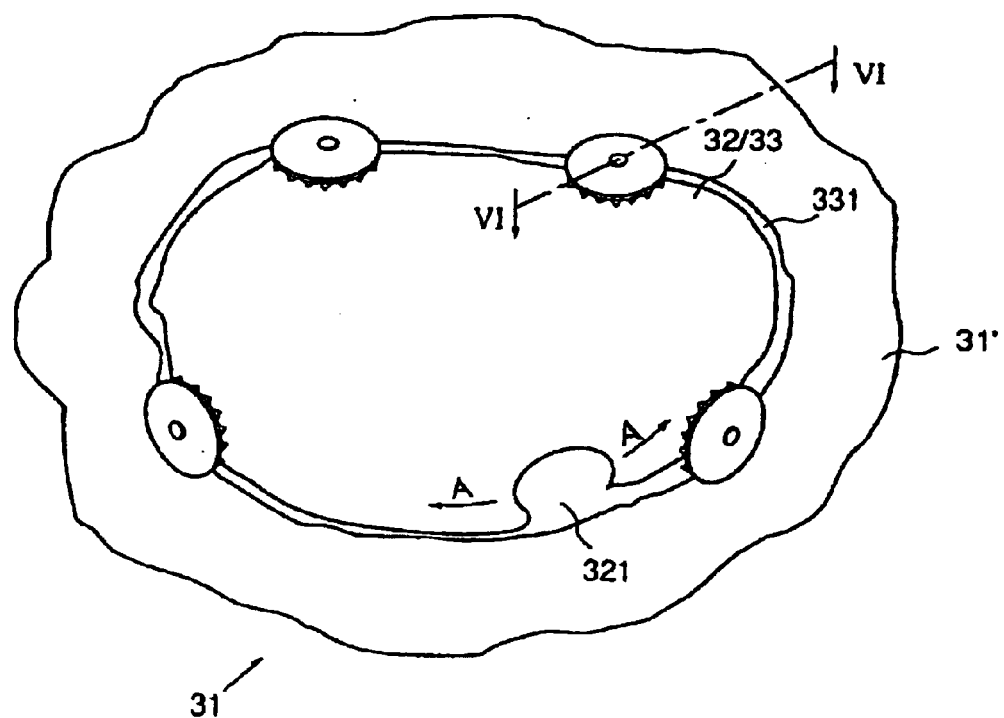
FIG. 5 illustrates how the device in accordance with the present invention can be employed.
Figure 6:
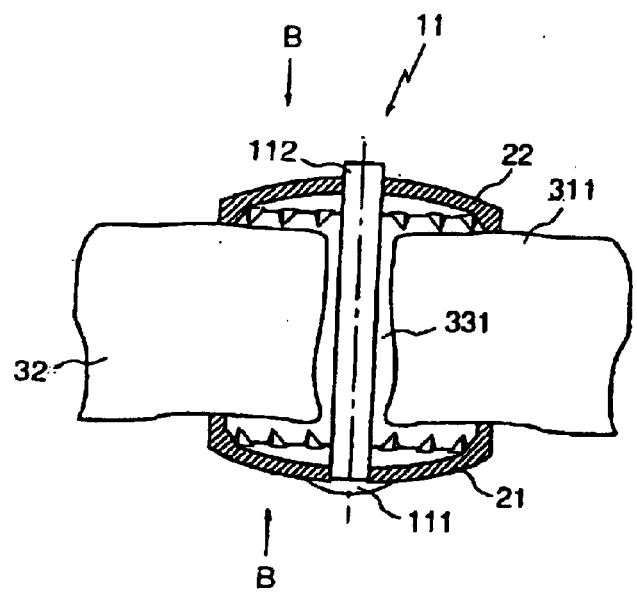
FIG. 6 is a section along the line VI—VI in FIG. 5.

FIGS. 5 and 6 illustrate how the device is employed. FIG. 5 illustrates part of an adult cranium 31 from which a plug 32 of bone has been sawn to provide access to the brain, which is available to the surgeon through aperture 33. A recess 321 slightly larger than the disks has been removed from plug 32 at its circumference, once the operation is over, the plug is returned to the aperture 33. Inner disks 22 are mounted on the shafts 112 of pins 11. The inner disks are inserted one by one through recess 321 with the shafts projecting out and slid along the inner surface of the plug and residual cranium with the shafts extending out of kerf 331 in the directions indicated by arrows A in FIG. 5 until they arrive at the point where they are to be positioned, outer disks 22 are now mounted on the shafts of the pins in situ. The outer disks are finally secured to the shafts with a tool of the type employed to fasten blind rivets. The tool forces outer disks 22 and inner disks 21 together in the direction indicated by arrow B in FIG. 6 until the teeth on each disk bite into the tissue of the plug and of the residual cranium, securing the two together. The section of each shaft extending out beyond the outer disk is now trimmed off The shaft can alternatively be threaded, and the disks forced together over the threads until the teeth bite into the tissue.

Figure 7:
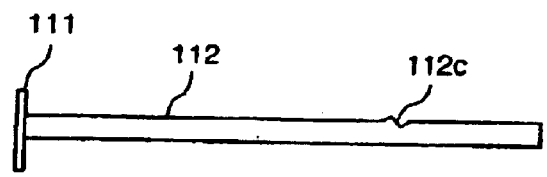
FIG. 7 is a schematic view and shows another embodiment of the present invention.
Figure 9:
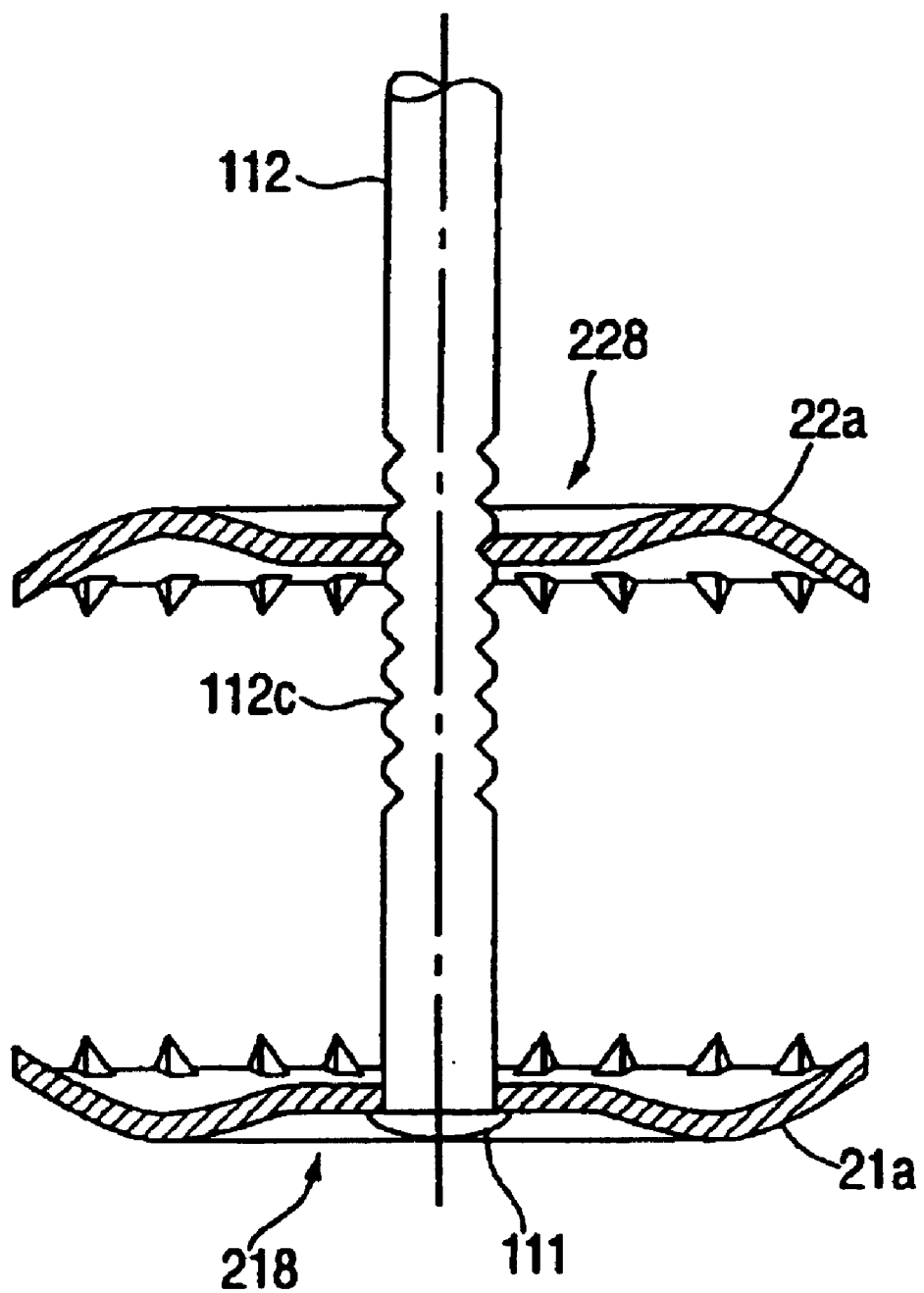
FIG. 9 is a longitudinal section of another embodiment of a device in accordance with the present invention.

Thus, in another embodiment shown in FIG. 7, as well as in FIG. 9, the shaft 112 of the pin 11 has notches 112c engaging the outer surface of the second disk 22 and forcing it towards the head 111 of the pin.

Figure 8:
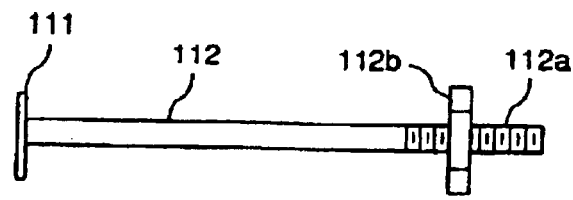
FIG. 8 is a schematic view of a still further embodiment according to the present invention.

In the embodiment of FIG. 8, the shaft of the pin 11 has a thread 112a and accommodates a nut 112b that can be screwed against the second disk 22.

In the embodiment shown in FIG. 9, the first disk 21a and the second disk 22a are each formed in a generally concavoconvex shape with a center portion 218, 228 of the disk being depressed in a direction opposite that of its concavoconvexity.

What is claimed is:

1. A cranial bone plug fixation device for fixing a plug of bone to surrounding cranial bone, the plug of bone having been removed during a surgical operation, the fixation device being formed of a physiologically compatible metallic substance and comprising:
   a pin having a shaft and a head at one end;
   first means for engaging internal surfaces of the plug of bone and the surrounding cranial bone, said first means having a central opening to receive therethrough the shaft of the pin, the first means to be mounted on the shaft at the one end of the pin; and
   second means for engaging external surfaces of the plug of bone and the surrounding cranial bone, said second means having a central opening to receive therethrough the shaft of the pin, the second means to be mounted on the shaft of the pin;
   wherein the shaft of the pin extends through the space between the plug of bone and the surrounding cranial bone and said first and second means grip between them the plug of bone and the surrounding cranial bone.

2. The fixation device of claim 1 wherein the first means comprises a first disk, and the second means comprises a second disk.

3. The device of claim 2 wherein the first disk has a generally concavoconvex shape.

4. The device of claim 3 wherein the first disk comprises a center portion depressed in a direction opposite that of the concavoconvexity of the first disk.

5. The device of claim 2 wherein the second disk has a generally concavoconvex shape.

6. The device of claim 5 wherein the second disk comprises a center portion depressed in a direction opposite that of the concavoconvexity of the first disk.

7. The device of claim 2 wherein the shaft has a plurality of notches to secure the second disk relative to the shaft to grip cranial bone plug and the adjacent cranial bone section between the first and second disks.

8. The device of claim 2 wherein the first disk comprises a plurality of protrusions formed substantially around a periphery thereof to engage the cranial bone plug and the adjacent cranial bone section.

9. The device of claim 2 wherein the second disk comprises a plurality of protrusions formed substantially around a periphery thereof to engage the cranial bone plug and the adjacent cranial bone section.

10. The device of claim 2 wherein the second disk comprises a plurality of slits extending radially outward from the central opening of the second disk.

11. A device for fixing a plug of bone to surrounding cranial bone, the plug of bone having been removed during a surgical operation, the device being formed of a physiologically compatible metallic substance and comprising:
    an elongated shaft formed of a physiologically compatible metallic substance;
    first means for engaging internal surfaces of the plug of bone and the surrounding cranial bone, said first means being formed of a physiologically compatible metallic substance and adapted to be attached at one end of the elongated shaft; and
    second means for engaging external surfaces of the plug of bone and the surrounding cranial bone, said second means being formed of a physiologically compatible metallic substance and having an opening extending therethrough to permit the elongated shaft to be inserted through the second means, the second means adapted to be mounted on the elongated shaft with the elongated shaft extending through the opening of the second means to hold a portion of the plug of bone and the surrounding cranial bone securely in place between the first means and second means.

12. The device of claim 11 wherein the elongated shaft comprises: a securing mechanism.

13. The device of claim 12 wherein the securing mechanism comprises:

a plurality of notches to engage the second means.

14. The device of claim 11 wherein the first means is an inner fastening element in the form of a disk.

15. The device of claim 14 wherein the inner fastening element is substantially circular in shape.

16. The device of claim 11 wherein the first means is an inner fastening element that comprises a plurality of protrusions formed substantially around a periphery thereof to engage the cranial bone plug and the adjacent cranial bone section.

17. The device of claim 11 wherein the second means is an outer fastening element in the form of a disk.

18. The device of claim 17 wherein the outer fastening element is substantially circular in shape.

19. The device of claim 11 wherein the second means is an outer fastening element that comprises a plurality of protrusions formed substantially around a periphery thereof to engage the cranial bone plug and the adjacent cranial bone section.

20. The device of claim 11 wherein the second means is an outer fastening element that comprises a plurality of slits extending radially outward from the opening of the outer fastening element.

21. A cranial bone flap reattachment device for fixing a plug of bone to surrounding cranial bone, the plug of bone having been removed during a surgical operation, the device being formed of a physiologically compatible metallic substance and comprising:

a pin including an elongated shaft with a substantially flat head at one end;

first means for engaging internal surfaces of the plug of bone and the surrounding cranial bone, said first means having an inner surface and an outer surface with an opening therebetween, the first means to be mounted on the pin so that the substantially flat head abuts the outer surface of the first means; and second means for engaging external surfaces of the plug of bone and the surrounding cranial bone, said second means having an inner surface and an outer surface with an opening therebetween, the pin adapted to be inserted through the opening of the second means and the second means adapted to be mounted on the shaft of the pin so the inner surfaces of the first and second means face each other and grip between the first and second means the plug of bone and the surrounding cranial bone.

22. The cranial bone flap reattachment device of claim 21 wherein the second means is adapted to engage a securing mechanism on the elongated shaft of the pin to grip the cranial bone flap and the adjacent section of the cranial bone between the first means and the second means.

23. The cranial bone flap reattachment device of claim 21 wherein each of the first and second means is a disk having a generally concavoconvex shape.

24. The cranial bone flap reattachment device of claim 21 wherein the second means is a disk comprising a plurality of slits extending radially outward from the opening of the second means.

* * * * *

UNITED STATES PATENT AND TRADEMARK OFFICE
CERTIFICATE OF CORRECTION

PATENT NO. : 6,962,591 B2
DATED : November 8, 2005
INVENTOR(S) : Karl-Dieter Lerch It is certified that error appears in the above-identified patent and that said Letters Patent is hereby corrected as shown below:

<u>Title page,</u>
Item [76], Inventor, "Nordstrasse 16, D-58452 Bundesrepublik (DE)" should read
-- Nordstrasse 16, D-58452 Witten, Bundesrepublik (DE) --.

Signed and Sealed this

Twenty-third Day of May, 2006

JON W. DUDAS
*Director of the United States Patent and Trademark Office*